United States Patent [19]
Geffard

[11] Patent Number: 6,114,388
[45] Date of Patent: Sep. 5, 2000

[54] MONOFUNCTIONAL AND/OR POLYFUNCTIONAL POLYLYSINE CONJUAGES

[76] Inventor: Michel Geffard, 200, avenue de Thouars, 33400 Talence, France

[21] Appl. No.: 08/836,199

[22] PCT Filed: Nov. 17, 1995

[86] PCT No.: PCT/FR95/01517

§ 371 Date: Jul. 9, 1997

§ 102(e) Date: Jul. 9, 1997

[87] PCT Pub. No.: WO96/15810

PCT Pub. Date: May 30, 1996

[30] Foreign Application Priority Data

Nov. 18, 1994 [FR] France .................. 94 13861

[51] Int. Cl.⁷ ............ A01N 37/12; A61K 38/00
[52] U.S. Cl. ............................. 514/563; 514/12
[58] Field of Search ................... 514/12, 563

[56] References Cited

FOREIGN PATENT DOCUMENTS

| | | |
|---|---|---|
| 79 00515 | 8/1979 | WIPO . |
| 91 13097 | 9/1991 | WIPO . |
| 92 16221 | 10/1992 | WIPO . |
| 93 25197 | 12/1993 | WIPO . |

OTHER PUBLICATIONS

Hammermeister et al. Biochim. Biophys. Acta, 332 (2), 125–130 (Abstract), 1974.
Kawai et al. J. Macromol. Sci., Phys., B 17 (4), 653–81 (Abstract), 1980.
Citro et al., *Br. J. Cancer* (1994), 69(3), 463–7.
Kammeyer et al., *Journal of Immunological Methods* (1992), 156, 61–67.
Seguela et al., *Pro. Natl. Acad. Sci.* USA (1984), 81, 3888–3892.
Campistron et al., *Brain Research* (1), 179–84.

*Primary Examiner*—Dwayne C. Jones
*Attorney, Agent, or Firm*—Bacon & Thomas

[57] ABSTRACT

A method of treating neurodegenerative diseases, infectious, traumatic or toxic neuropathies, degenerative diseases of the autoimmune type, neurodegenerative disorders resulting from genetic diseases or proliferative diseases with polylysine conjugates is disclosed. Polylysine conjugates are also disclosed.

16 Claims, No Drawings

MONOFUNCTIONAL AND/OR POLYFUNCTIONAL POLYLYSINE CONJUAGES

This application is a 371 of PCT/FR95/01517, filed on Nov. 17, 1995.

The present invention relates to the medical sector. More particularly, the invention relates to the use of at least one monofunctional and/or polyfunctional polylysine conjugate for the preparation of pharmaceutical compositions or combinations which are useful in the treatment of neuronal degeneration, infectious, traumatic and toxic neuropathies, degenerative diseases of the autoimmune type, neurodegenerative disorders resulting from genetic diseases, and proliferative diseases. The invention further relates to monofunctional and polyfunctional polylysine conjugates.

The majority of incapacitating chronic human diseases, such as multiple sclerosis (MS), polyarthritis (RP), neuropathy, etc., do not have a clearly defined etiology. Consequently the treatments currently practiced are still symptomatic: use of corticoids, various anti-inflammatories, immunodepressants, etc.; these medications have a large number of appreciable side effects on the patients' health. Furthermore they are of transient efficacy. No lasting improvement is observed and, in particular, there is little notable improvement in the course of these diseases.

Recent data and studies on autoimmunity (Daverat et al., 1989 (1), Amara et al., 1994 (2)) have made it possible to identify chemically defined antigenic targets by the antibodies circulating in the patients' biological fluids. The increase in these circulating immunoglobulins is linked to the course of these diseases. The antibodies no longer appear as aberrant elements but are the reflection of precise antigenic disorders.

By way of example, antibodies directed against conjugated oleic acid, conjugated azelaic acid, a phospholipid and cysteinyl-NO have been identified in MS (Maneta-Peyret et al., 1987 (3); Daverat et al., 1989 (1); Brochet et al., 1991 (4); Boullerne et al., 1994 (5)).

Similarly, in the case of infection with HIV, antibodies directed against fatty acids coupled by an amide linkage have been found (Amara et al., 1994 (2)).

Patent application WO 94/27151, published on Nov. 24, 1994, describes the use of at least one conjugate between on the one hand a molecule capable of being recognized by:
the antibodies directed against saturated or unsaturated, linear or branched $C_4$–$C_{22}$ fatty acids;
the antibodies directed against $C_6$–$C_{20}$ isoprenoids bonded to a cysteine; and/or
the antibodies directed against cholesterol and its derivatives, and on the other hand a molecule of sufficient size to allow its recognition by said antibodies, such as polylysine, for the preparation of drugs intended for the treatment of AIDS.

The following have also been described: an antibody directed against choline-glutaryl-poly-L-lysine, which mimics acetylcholine (Geffard et al., 1985 (11); Souan et al., 1986 (12)), R-glutaraldehyde-polylysine antisera, in which R is an indolealkylamine compound, which are directed against indolealkylamines (Geffard et al., 1985 (13)), and antibodies directed against γ-aminobutyric acid (Geffard et al., 1985 (14); Seguela et al., 1984 (15)) and an aspartate-polylysine conjugate used in the immunochemical characterization of polyclonal antibodies directed against conjugated aspartate (Campistron et al., 1986 (21)).

Oxidative processes have been found in the course of the chronic diseases mentioned above and have been described (Buttke et al., 1994 (6)). Thus, in MS, authors have shown a direct increase in the lipoperoxidation products (Hunter et al., 1985 (7), Korpela et al., 1989 (8)) and a notable drop in the antioxidants.

Recent data have shown that, in the course of HIV infection, oxidative stress is one of the determining factors in cell death, i.e. the loss of TCD4$^+$ lymphocytes (Roederer et al., 1993 (9), Staal et al., 1992 (10)).

It was therefore essential to provide patients with drugs having the following three objectives:
to restore the antigenic perturbations specifically identified during a chronic human disease;
to control the oxidative inflammatory processes;
to inhibit the viral and/or bacterial etiological agents capable of causing progressive chronic diseases.

The Applicant has solved this problem by using monofunctional and/or polyfunctional poly-L-lysine conjugates for therapeutic purposes.

According to a first feature, the present invention therefore relates to the use of at least one monofunctional and/or polyfunctional poly-L-lysine conjugate for the preparation of pharmaceutical compositions or combinations which are useful in the treatment of neuronal degeneration, infectious, traumatic or toxic neuropathies, degenerative diseases of the autoimmune type, neurodegenerative disorders resulting from genetic diseases, and proliferative diseases.

Poly-L-lysine (hereafter called polylysine) is a lysine polypeptide or homopolymer, the chain length of which varies with the method of preparation. It has the formula

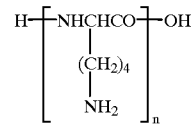

(cf. Merck Index, 10th edition, abstract no. 7444). This product has an average molecular weight generally of between 2000 and 300,000, signifying that its degree of polymerization (i.e. the value of the index n above) is between about 15 and about 2345. Polylysine is of course understood as meaning linear or branched polylysine. It is advantageous according to the present invention to use linear polylysine having an average molecular weight of between 20,000 and 30,000.

Monofunctional and polyfunctional polylysine conjugates are understood as meaning the products resulting from the coupling of any one of the molecules defined below with polylysine and, respectively, the products resulting from the coupling of at least two molecules defined below with at least one molecule of polylysine. For example, a bifunctional conjugate can be represented by the formula molecule 1—polylysine—molecule 2

The polyfunctional conjugates used within the framework of the invention are advantageously bifunctional conjugates.

The molecules used within the framework of the invention, denoted by the term "haptens" in the Preparations below, can be selected from one of the following three categories:

1/Molecules of the "fatty acid or lipid" type comprising:
monocarboxylic or dicarboxylic fatty acids, hereafter commonly denoted by the term fatty (di)acids, which are linear or branched and saturated or unsaturated and generally comprise from 4 to 24 carbon atoms;

compounds involved in the mechanism of anchoring of proteins to cell membranes, these compounds participating especially in the mevalonate cycle, particularly isoprenoids bonded to a cysteine;

cholesterol and its derivatives, especially hydrophobic hormones.

2/Molecules of the "antioxidant" type comprising:

vitamin A, vitamin C, vitamin E or one of their derivatives;

cysteine and its derivatives of the formula $$R_1S\text{---}R_2\text{---}CH(NH_2)\text{---}COOH$$

in which $R_1$ is H or $CH_3$ and $R_2$ is a $C_1$–$C_3$-alkylene.

3/Molecules of the "amino acid or neurotransmitter" type comprising:

indolealkylamines;

catecholamines;

amino acids of the formula $$R_3\text{---}CH(NH_2)\text{---}COOH$$

in which $R_3$ is hydrogen, an imidazol-5-ylmethyl group, a carboxymethyl group or an aminopropyl group;

amino($C_1$–$C_5$)alkylsulfonic or sulfinic acids;

carnitine or carnosine;

diamines of the formula $$H_2N\text{---}A\text{---}NH_2$$

in which A is a ($C_1$–$C_6$)alkylene or a group —$(CH_2)_m$—NH—B—$(CH_2)_p$—, in which m and p independently of one another are integers ranging from 1 to 5 and B is nothing or a group —$(CH_2)_n$—NH—, n being an integer ranging from 1 to 5;

acetylcholine; and

γ-aminobutyric acid.

There will therefore be three different kinds of conjugates (whether they be monofunctional or polyfunctional): "fatty acid or lipid" conjugates; "antioxidant" conjugates; and "amino acid or neurotransmitter" conjugates.

In one variant of the invention, at least 4 monofunctional and/or polyfunctional polylysine conjugates are used for the preparation of pharmaceutical compositions or combinations for the treatment of the disorders mentioned above. It is possible only to use conjugates of the same kind. It is advantageous to use conjugates of two different kinds. It is preferable to use conjugates of each of the three kinds above.

In another variant of the invention, it is possible also to use one or two anti-idiotypic monoclonal antibodies for the preparation of the pharmaceutical compositions or combinations mentioned above. Examples of these antibodies are those described by Chagnaud et al. (18, 19, 20).

The fatty (di)acid generally comprises from 4 to 24 carbon atoms, for example butyric, maleic, succinic, glutaric, adipic, pimelic, suberic, sebacic, caproic, caprylic, capric, lauric, myristic, palmitic, palmitoleic, stearic, oleic, linoleic, γ-linolenic, α-linolenic, arachidic, gadoleic, arachidonic, bethenic, erucic, clupadonic or azelaic acid. The fatty (di)acid is preferably selected from myristic acid, palmitic acid, stearic acid, oleic acid and azelaic acid.

The isoprenoids bonded to a cysteine generally comprise from 6 to 20 carbon atoms. Within the framework of the invention it is advantageous to use farnesylcysteine, geranylgeranylcysteine or mevalonatecysteine.

The hydrophobic hormone used is advantageously progesterone or 2-methoxyestradiol.

The cysteine derivative used is advantageously homocysteine or methionine.

The indolealkylamines and catecholamines used within the framework of the invention include especially tryptophan, 5-methoxytryptophan, serotonin, tryptamine, 5-methoxytryptamine, melatonin, phenylalanine, 3,4-dihydroxyphenylalanine and tyrosine.

The amino acids used are preferably histidine, glycine, aspartate or ornithine.

The amino($C_1$–$C_5$)alkylsulfonic or sulfinic acids used according to the invention include especially taurine, homotaurine and hypotaurine.

The diamines which are preferably used within the framework of the invention are putrescine, cadaverine, spermine and spermidine.

The molecule used in the monofunctional polylysine conjugates is advantageously a fatty (di)acid as defined above. At least one of the molecules used in the polyfunctional polylysine conjugates is advantageously a fatty (di) acid as defined above, it being understood that several different fatty (di)acids can be used. Said fatty (di)acid is preferably selected from myristic acid, palmitic acid, stearic acid, oleic acid and azelaic acid.

According to another feature, the invention further relates to the food and vitamin complements which comprise, as the active principle, at least one monofunctional and/or polyfunctional polylysine conjugate defined above, especially at least one conjugate between a fatty (di)acid and polylysine.

The methods of coupling between said molecules and polylysine to give these conjugates are the conventional methods, well known to those skilled in the art, of chemical coupling between a functional group of each molecule and a functional group of the polylysine. These coupling reactions are effected via a coupling agent selected for example from glutaraldehyde, succinic or glutaric anhydride, carbodiimide, ethyl chloroformate and hexamethylene diisocyanate. Particular examples of such coupling methods are those described in Geffard et al. (16). The molecules can also be coupled with the polylysine by simple adsorption. Examples of appropriate coupling methods are described in detail in the Preparations below.

As an illustration, the coupling between said molecules and the polylysine can be effected between an amine group of the polylysine and a carboxyl group of said molecules.

Thus, in the case of fatty acids, especially myristic acid, palmitic acid, etc., and in the case of isoprenoids bonded to a cysteine, especially farnesylcysteine, the linkage with the polylysine is effected between an amine group of the latter and the carboxyl group of the above-mentioned molecules.

Likewise, in the case of cysteine and its derivatives, the linkage with the polylysine is advantageously effected between an amine group of the latter and the acid group of these molecules.

Alternatively, the cysteine and its derivatives can be activated beforehand by coupling with succinic or glutaric anhydride, the linkage then being formed between an amine group of the polylysine and the free acid group of the succinylated or glutarylated molecule. As a further possibility, the cysteine and its derivatives can be bonded to the polylysine by reaction with glutaraldehyde, the reaction taking place especially as described by Geffard et al. (17).

In the case of cholesterol and its derivatives, the coupling with the polylysine is advantageously effected via the hydroxyl group of the cholesterol.

The cholesterol and its derivatives are advantageously adsorbed onto the polylysine.

In the case of hydrophobic hormones, the coupling with the polylysine is advantageously effected via hexamethylene diisocyanate.

In the case of vitamin A (retinoic acid), the linkage between this molecule and the polylysine is effected between the amine group of the latter and the acid group of the molecule.

In the case of vitamin C (ascorbic acid), the linkage between this molecule and the polylysine is effected between the amine group of the latter and the oxo group of the molecule.

In the case of vitamin E (α-tocopherol), the linkage between this molecule and the polylysine is effected between the amine group of the latter and the free acid group of the acid succinate of the molecule.

In the case of aminoalkylsulfonic or sulfinic acids, especially taurine, homotaurine and hypotaurine, the linkage between these molecules and the polylysine is effected by prior activation of the molecules with an acid anhydride (succinic or glutaric anhydride) or else by coupling with glutaraldehyde.

In the case of amino acids, certain indolealkylamine compounds, especially tryptophan, and catecholamines, the linkage between these molecules and the polylysine can be effected either directly or by coupling with carbodiimide, glutaraldehyde, an acid anhydride or an acid chloride, for example ethyl chloroformate.

In the case of diamines, the linkage between these molecules and the polylysine can be effected by coupling with glutaraldehyde or an acid anhydride. The linkage between carnitine or carnosine, on the one hand, and polylysine, on the other, is effected by coupling with carbodiimide.

The conjugates according to the invention can be used especially for the preparation of pharmaceutical compositions or combinations which are useful in the treatment of neuronal degeneration, infectious, traumatic and toxic neuropathies, degenerative diseases of the autoimmune type, neurodegenerative disorders resulting from genetic diseases, and proliferative diseases, and more particularly in the following indications: memory disorders, vascular dementia, postencephalitic disorders, postapoplectic disorders, post-traumatic syndromes due to a cranial traumatism, disorders derived from cerebral anoxia, Alzheimer's disease, senile dementia, subcortical dementia such as Huntington's chorea and Parkinson's disease, dementia caused by AIDS, neuropathies derived from morbidity or damage to the sympathetic or sensory nerves, brain diseases such as cerebral edema, spinocerebellar degenerations, neuropathies resulting from Lyme disease, diseases presenting neurodegenerative disorders, such as Charcot-Marie-Tooth disease, amyotrophic lateral sclerosis, multiple sclerosis, epilepsy, migraine, polyarthritis, insulin-dependent diabetes, systemic lupus erythematosus, Hashimoto's thyroiditis, Horton's disease, dermatomyositis and polymyositis, as well as ankylosing spondylarthritis, HIV infection and cancer.

The invention further relates to a method of treating these diseases with the polylysine conjugates defined above.

Within the framework of the present invention, pharmaceutical combination is understood as meaning several mixtures of polylysine conjugates, individually packaged, which can be administered simultaneously or separately, for example sequentially. These mixtures are presented in identical or different individual packs in combination with a pharmaceutically acceptable vehicle. The pharmaceutical compositions according to the invention contain, as the active principle, a mixture of polylysine conjugates as defined above, in combination with a pharmaceutically acceptable vehicle.

The conjugates according to the invention are preferably administered parenterally. The amount of active principle to be administered in the treatment of the above disorders by the method of the present invention quite obviously depends on the nature and severity of the diseases to be treated and also on the patient's weight. Nevertheless the preferred unit doses will generally comprise from 0.1 to 2 ml, preferably from 0.5 to 1 ml, for example 0.6, 0.8 and 1 ml, of conjugate solution at a rate of 0.3 to 0.6 mg conjugates/ml. These unit doses will normally be administered 1 to 4 times a day, but it is also possible to envisage administering them at longer intervals of time, for example every 2 to 3 days.

The conjugates according to the invention can be presented in the form of aqueous solutions containing the unit doses indicated above in an isotonic or sterile aqueous vehicle optionally containing biocompatible dispersants and/or wetting agents. These solutions are packaged in an appropriate manner to allow parenteral administration, for example intravenous, intramuscular or subcutaneous administration, or introduction into an intravenous perfusion device, or else administration by an implant system permitting subcutaneous perfusion.

The conjugates according to the invention can also be administered orally, intranasally, rectally or transdermally. In this case, the unit forms of administration are prepared in conventional manner by the conventional techniques known to those skilled in the art, with the excipients commonly used in this field.

The following may be mentioned as examples of pharmaceutical compositions according to the invention (the abbreviations used are explained below):

- a composition comprising the following conjugates: L-DOPA-G-PL, αtoco-PL, Ole-PL-Farcys, PO-PL-Ole, Myr-PL-Ole, Cys-GA-PL or Cys-SA-PL, Homocys-GA-PL or Homocys-SA-PL, Met-GA-PL or Met-SA-PL, Met-G-PL, Cys-G-PL, Homocys-G-PL, Laur-PL-Ole, GABA-GA-PL, 5MT-GA-PL, His-PL, Cys-PL-Nac, Homocys-PL-Nac and Met-PL-Nac, which is useful especially for the treatment of Parkinson's disease.
- a composition comprising the following conjugates: GABA-G-PL, PO-PL-Aze, Pal-PL-Farcys, Myr-PL-Farcys, W-GA-PL, Ole-PL-Pal, Myr-PL-Ole, αtoco-PL and Aze-PL-Lin2, which is useful especially for the treatment of epilepsy.
- a composition comprising the following conjugates: HW-GA-PL, W-GA-PL, MT-GA-PL, αtoco-PL, Cys-GA-PL, Met-GA-PL and Homocys-GA-PL, which is useful especially for the treatment of essential migraine.

The following may be mentioned as examples of pharmaceutical combinations according to the invention:

- a combination comprising, in two individual packs, on the one hand the following conjugates (1a): Farcys-PL-Pal, Pal-PL-Myr, Farcys-PL-Myr, Lin2-PL-Ole, Met-PL-Nac, Cys-PL-Nac, Homocys-PL-Nac, Farcys-PL-Ole, Met-GA-PL, Pal-PL-Ole, Myr-PL-Ole, Tau-GA-PL, VitC-PL, Tau-G-PL, Stea-PL-Farcys, ACh-GA-PL, αtoco-PL and Aze-PL-Ole; and on the other hand the following conjugates (1b): Farcys-PL-Pal, Farcys-PL-Myr, Pal-PL-Myr, Aze-PL-Ole, Pal-PL-Ole, Farcys-PL-Ole, PO-PL-Aze, Ole-PL-Myr, Stea-PL-Farcys and Ole-PL-Laur, which is useful especially for the treatment of post-Lyme neuropathies and ankylosing spondylarthritis.
- a combination comprising, in two individual packs, on the one hand the following conjugates (2a): Myr-PL-Pal, Pal-PL-Ole, Myr-PL-Ole, Tau-SA-PL or Tau-GA-PL, αtoco-PL, VitC-PL, Homocys-PL-Nac, Cys-PL-Nac, Met-PL-Nac, Farcys-PL-Myr, Farcys-PL-Pal, Farcys-PL-Ole, Farcys-PL-Stea, Met-SA-PL or Met-GA-PL, Homocys-SA-PL or Homocys-GA-PL, Cys-G-PL, Homocys-G-PL, Met-G-PL, CHO-PL, 5MT-GA-PL, W-GA-PL and ACh-GA-PL; and on the other hand the following conjugates (2b): Pal-PL-Ole, Tau-SA-PL or Tau-GA-PL, αtoco-PL, VitC-PL, Homocys-PL-Nac, Cys-PL-Nac, Met-PL-Nac, Farcys-PL-Myr, Farcys-PL-Pal, Farcys-PL-Ole, Farcys-PL-Stea, Met-SA-PL or Met-GA-PL, Homocys-SA-PL or Homocys-GA-PL, Cys-GA-PL, Cys-G-PL, Met-G-PL, Homocys-G-PL, Met-G-PL, CHO-PL, W-GA-PL and ACh-GA-PL, which is useful especially for the treatment of amyotrophic lateral sclerosis.

a combination comprising, in three individual packs:
3a) the following conjugates: Myr-PL-Pal, Pal-PL-Ole, Myr-PL-Ole, Tau-SA-PL or Tau-GA-PL, αtoco-PL, VitC-PL, Homocys-PL-Nac, Cys-PL-Nac, Met-PL-Nac, Farcys-PL-Myr, Farcys-PL-Pal, Farcys-PL-Ole, Farcys-PL-Stea, Met-SA-PL or Met-GA-PL, Homocys-SA-PL or Homocys-GA-PL, Cys-G-PL, Homocys-G-PL, Met-G-PL, CHO-PL, 5MT-GA-PL, W-GA-PL and ACh-GA-PL;
3b) the following conjugates: Cys-GA-PL, Met-GA-PL, Homocys-G-PL, Cys-PL-Nac, Homocys-PL-Nac, Met-PL-Nac, Tau-GA-PL, Tau-G-PL, Met-G-PL, αtoco-PL and αtoco-PL-Ret; and
3c) the following conjugates: Farcys-PL-Ole, Aze-PL-Ole, Aze-PL-PO, Met-PL-Nac, Cys-PL-Nac, Homocys-PL-Nac, αtoco-PL, Lin2-PL-Ole, Ret-PL, Ole-PL-Laur, αtoco-PL-Ret, Tau-G-PL, ACh-GA-PL, PRO-PL and GABA-G-PL,
which is useful especially for the treatment of Huntington's chorea.

a combination comprising, in four individual packs:
4a) the following conjugates: Farcys-PL-Ole, PO-PL-Ole, Aze-PL-Ole, Aze-PL-PO, Met-PL-Nac, Homocys-PL-Nac, αtoco-PL, VitC-PL, Tau-GA-PL, Lin2-PL-Ole, CHO-PL, Ole-PL-Laur, 5MT-GA-PL, Tau-G-PL and ACh-GA-PL;
4b) the following conjugates: Farcys-PL-Pal, Farcys-PL-Myr, Pal-PL-Myr, Aze-PL-Ole, Pal-PL-Ole, Farcys-PL-Ole, PO-PL-Aze, Ole-PL-Myr, Stea-PL-Farcys and Ole-PL-Laur;
4c) the following conjugates: Farcys-PL-Ole, Aze-PL-Ole, Aze-PL-PO, Met-PL-Nac, Cys-PL-Nac, Homocys-PL-Nac, αtoco-PL, Lin2-PL-Ole, Ret-PL, Ole-PL-Laur, αtoco-PL-Ret, Tau-G-PL, ACh-GA-PL, PRO-PL and GABA-G-PL; and
4d) the following conjugates: Farcys-PL-Ole, Aze-PL-Ole, Aze-PL-PO, αtoco-PL, VitC-PL, Tau-GA-PL, Lin2-PL-Ole, CHO-PL and Laur-PL-Ole, which is useful especially for the treatment of multiple sclerosis.

a combination comprising, in three individual packs:
5a) the following conjugates: Farcys-PL-Pal, Pal-PL-Myr, Farcys-PL-Myr, Lin2-PL-Ole, Met-PL-Nac, Cys-PL-Nac, Homocys-PL-Nac, Farcys-PL-Ole, Met-GA-PL, Pal-PL-Ole, Myr-PL-Ole, Tau-GA-PL, VitC-PL, Tau-G-PL, Stea-PL-Farcys, ACh-GA-PL, αtoco-PL and Aze-PL-Ole;
5b) the following conjugates: Farcys-PL-Pal, Farcys-PL-Myr, Pal-PL-Myr, Aze-PL-Ole, Pal-PL-Ole, Farcys-PL-Ole, PO-PL-Aze, Ole-PL-Myr, Stea-PL-Farcys and Ole-PL-Laur; and
5c) the following conjugates: Farcys-PL-Pal, Pal-PL-Myr, Farcys-PL-Myr, Farcys-PL-Ole, Myr-PL-Ole, Stea-PL-Farcys, ACh-GA-PL and αtoco-PL, which is useful especially for the treatment of polyarthritis.

a combination comprising, in two individual packs, on the one hand the following conjugates (6a): Lin2-PL-Farcys, Stea-PL-Farcys, Myr-PL-Farcys, Pal-PL-Farcys, Ole-PL-Farcys, Cys-GA-PL, Met-GA-PL, Homocys-GA-PL, CHO-PL, Homocys-PL-Nac, Cys-PL-Nac, αxtoco-PL-Ret, αtoco-PL, VitC-PL, Ole-PL-Laur, Met-G-PL, Met-PL-Nac, Homocys-PL-Nac and Cys-G-PL; and on the other hand the conjugates mentioned in section 3c) above, which is useful especially for the treatment of HIV infection.

a combination comprising, in three individual packs:
7a) the following conjugates: PRO-PL, Ret-PL, αtoco-PL, (xtoco-PL-Ret, W-GA-PL, 5MT-GA-PL and Hist-PL;
7b) the conjugates mentioned in section 1b) above; and
7c) the following conjugates: L-DOPA-G-PL, L-DOPA-GA-PL, 5MT-GA-PL, HW-GA-PL and Tyr-GA-PL,
which is useful especially for the treatment of cancer.

According to another feature, the invention further relates to the monofunctional and polyfunctional conjugates between on the one hand polylysine and on the other hand a molecule (several molecules) selected from:

saturated or unsaturated, linear or branched fatty (di)acids generally comprising from 4 to 24 carbon atoms;

the compounds involved in the mechanism of anchoring of proteins to cell membranes, these compounds participating especially in the mevalonate cycle, particularly isoprenoids bonded to a cysteine;

cholesterol and its derivatives, especially hydrophobic hormones;

vitamin A, vitamin C, vitamin E or one of their derivatives;

cysteine and its derivatives of the formula

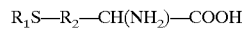

in which $R_1$ is H or $CH_3$ and $R_2$ is a $C_1$–$C_3$-alkylene;

indolealkylamines;

catecholamines;

amino acids of the formula

in which $R_3$ is hydrogen, an imidazol-5-ylmethyl group, a carboxymethyl group or an aminopropyl group;

amino($C_1$–$C_5$)alkylsulfonic or sulfinic acids;

carnitine or carnosine;

diamines of the formula

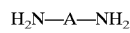

in which A is a ($C_1$–$C_6$)alkylene or a group —$(CH_2)_m$—NH—B—$(CH_2)_p$—, in which m and p independently of one another are integers ranging from 1 to 5 and B is nothing or a group —$(CH_2)_n$—NH—, n being an integer ranging from 1 to 5;

acetylcholine; and

γ-aminobutyric acid,
with the proviso that if the conjugate is monofunctional, the molecule is selected from:

a hydrophobic hormone;

vitamin A, vitamin C, vitamin E or one of their derivatives;

an amino acid of the formula

in which $R_3$ is hydrogen, an imidazol-5-ylmethyl group or an aminopropyl group;

an amino($C_1$–$C_5$)alkylsulfonic or sulfinic acid;

carnitine or carnosine; and a diamine of the formula

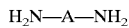

in which A is a ($C_1$–$C_6$)alkylene or a group —$(CH_2)_m$—NH—B—$(CH_2)_p$—, in which m and p independently of one another are integers ranging from 1 to 5 and B is nothing or a group —$(CH_2)_n$—NH—, n being an integer ranging from 1 to 5.

The Preparations and Examples which follow illustrate the invention without however limiting its scope.

The Preparations illustrate the synthesis of the conjugates, which are identified by the coupling agent used, and the Examples relate to the pharmaceutical compositions and combinations of the invention. The following abbreviations have been used in said Preparations and Examples:

5MT=5-methoxytryptamine;
ACh=acetylcholine;
GA=glutaric anhydride;
SA=succinic anhydride;
G=reduced glutaraldehyde;
αtoco=α-tocopherol;
Aze=azelaic acid;
CHO=cholesterol;
Cys=cysteine;
DMF=dimethylformamide;
DMSO=dimethyl sulfoxide;
ECF=ethyl chloroformate;
Farcys=farnesylcysteine;
GABA=γ-aminobutyric acid;
His=histamine;
Hist=histidine;
Homocys=homocysteine;
HW=5-hydroxytryptophan;
Laur=lauric acid;
L-DOPA=L-3,4-dihydroxyphenylalanine;
Lin2=α-linoleic acid;
SMB=sodium metabisulfite;
MES=morpholinoethanolsulfonic acid;
Met=methionine;
Myr=myristic acid;
Pal=palmitic acid;
Nac=N-acetylated;
Ret=retinoic acid;
Ole=oleic acid;
PO=palmitoleic acid;
Stea=stearic acid;
Tau=taurine;
TEA=triethylamine;
VitC=ascorbic acid;
W=tryptophan;
PRO=progesterone;
2ME=2-methoxyestradiol;
AI=anti-idiotypic monoclonal antibody;
PL=polylysine.

Preparations

I. Glutaraldehyde Conjugates:

This Preparation illustrates especially the preparation of the conjugates of cysteine or its derivatives with polylysine according to the following reaction scheme:

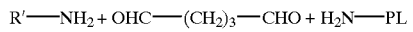

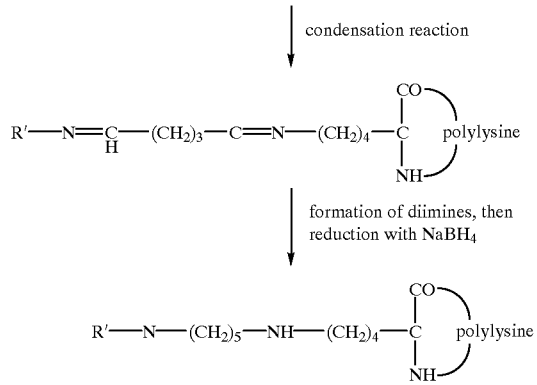

(R'=cysteinyl, homocysteinyl, methionyl)

20 mg of hapten are taken up with 1 ml of 1.5 M acetate buffer (pH 8) containing 1 μl of radioactive tracer ($^3$H-tyrosine; ref. NET 127, Dupont de Nemours). In the case of catecholaminergic conjugates, it is necessary to add a few grains of SMB. When tryptophan is used, it has to be solubilized in 1 ml of DMSO (Prolabo) and 1 ml of sodium acetate (Prolabo).

40 mg of polylysine are separately taken up with 2 ml of 1.5 M acetate buffer.

1 ml of 5% glutaraldehyde solution (Prolabo) is added to the hapten solution, followed after about 10 seconds by the polylysine. The coupling reaction produces a yellow coloration; as soon as this is obtained, the reaction is stopped by the addition of a few drops of $NaBH_4$ solution (Aldrich) (a few grains in water so as to give a solution which "bubbles").

In the particular case of taurine, it is necessary to add 1 ml of glutaraldehyde which is only 1%.

The conjugates are purified by dialysis against water, except in the case of catecholamines, where it is necessary to add SMB to the dialysis solution.

The resulting conjugates are designated R-G-PL (R=hapten, G=reduced glutaraldehyde residue).

II. Conjugates with a Succinyl or Glutaryl Arm

This is the case for example of α-tocopherol (vitamin E), cysteine and its derivatives, or else 5-methoxytryptamine, taurine and homotaurine:

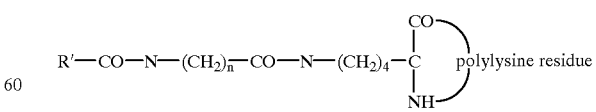

R'=cysteinyl, homocysteinyl or methionyl, n being 2 in the case of succinic acid or anhydride and 3 in the case of glutaric acid or anhydride.

αtoco-SA-PL

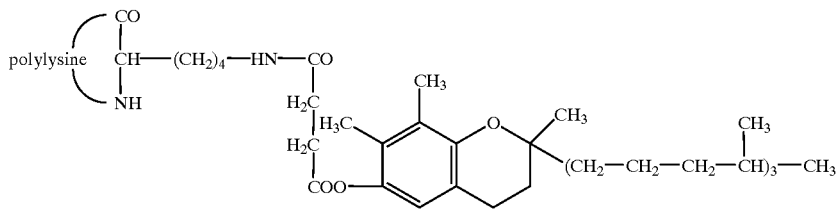

5MT-SA or GA-PL

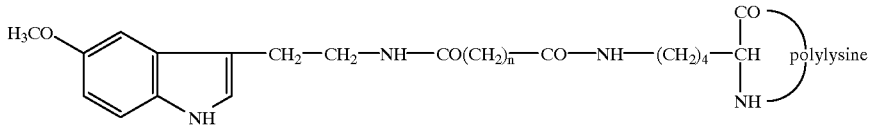

n = 2 or 3

(homo)tau-SA or GA-PL

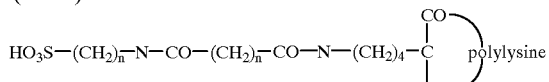

n = 2 or 3

40 mg of hapten are solubilized in 1 ml of water containing 1 µl of radioactive tracer ($^3$H-tyrosine). When 5-methoxytryptamine is used, it can only be solubilized by adding 200 µl of DMSO. 34 mg of glutaric or succinic anhydride (Sigma) are added, followed immediately by 340 µl of 1 M NaOH (Prolabo) to bring the pH to 7. The conjugates are then lyophilized.

These conjugates are attached to the polylysine by means of ethyl chloroformate (Fluka) at 4° C. The glutaryl- or succinyl-haptens are taken up with 1.6 ml of anhydrous DMF (Prolabo) and 20 µl of anhydrous TEA (Merck) (incomplete solubilization). The COOH groups are activated with 400 µl of ECF diluted 1/16 in anhydrous DMF for 5 minutes. PL solution (80 mg dissolved in 2 ml of water and 20 µl of anhydrous TEA) is then added.

The conjugates are purified by dialysis against water.

The resulting conjugates are designated R-SA or GA-PL (R=hapten, SA=succinyl residue, GA=glutaryl residue).

III. Carbodiimide Conjugates 50 mg of hapten and 50 mg of polylysine are solubilized in 1 ml of 0.2 M MES buffer, pH 5.4.

200 mg of carbodiimide (Sigma) are added gradually to this solution in about 10 minutes. The pH must be checked after each addition and adjusted to 5.4.

The conjugates are purified by dialysis against water.

The resulting conjugates are designated R-PL (R=hapten linked via —CO—NH—).

IV. Ethyl Chloroformate Conjugates (hydrophilic molecules)

VitC-PL:

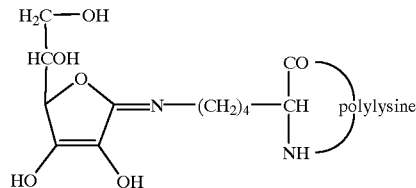

40 mg of hapten are taken up with 1.6 ml of anhydrous DMF and 20 µl of anhydrous TEA. The COOH groups are activated with 400 µl of ECF diluted 1/16 in anhydrous DMF for 5 minutes. PL solution (80 mg dissolved in 2 ml of water and 20 µl of anhydrous TEA) is then added.

Cysteine, homocysteine, methionine:

40 mg of hapten are taken up with 2 ml of anhydrous methanol and 20 µl of anhydrous TEA (difficult solubilization). The COOH groups are activated with 1 ml of ECF diluted 1/16 in anhydrous DMF for 5 minutes. After 5 minutes, PL solution (80 mg dissolved in 2 ml of water and 20 µl of anhydrous TEA) is added.

Carnitine:

Thorough dehydration of the carnitine is assured by lyophilization. The coupling must then be performed very rapidly because carnitine is very hygroscopic. The protocol is the same as for vitamin C.

The conjugates are purified by dialysis against water.

The resulting conjugates are designated R-PL (R=hapten).

V. Ethyl Chloroformate Conjugates (fatty acids, farnesylcysteine, retinoic acid and α-tocopherol)

Farnesylcysteine:

Farnesylcysteine results from the condensation of farnesol:

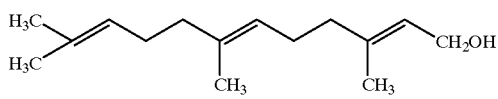

with cysteine:

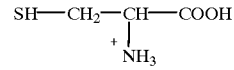

via a thioether linkage:

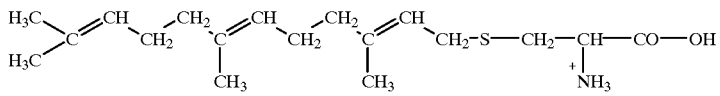

This molecule is then bonded to the polylysine:

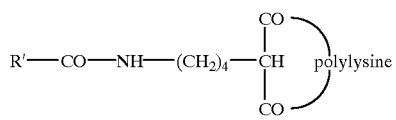

(R'=farnesylcysteine residue)

20 mg of hapten are used for fatty acids (40 mg for azelaic acid), 40 mg for farnesylcysteine, 40 mg for retinoic acid or 60 mg for α-tocopherol. The haptens are solubilized in 1 ml of anhydrous methanol and 20 μl of anhydrous TEA containing 1 μl of radioactive label ($^{14}$C-palmitic acid: ref. C14 NECQ, Dupont de Nemours). The mixture is then left to stand under a dry atmosphere for 30 minutes.

This mixture is then activated with 200 μl of ethyl chloroformate diluted 1/16 in anhydrous DMF for 15 minutes at 4° C. PL solution (80 mg in 4 ml of $10^{-2}$, M phosphate buffer containing $10^{-3}$ M $CaCl_2$ and 40 μl of anhydrous TEA) is then added.

When the reaction has ended, the conjugate is purified by dialysis. The solutions obtained are transferred to dialysis tubes (Visking dialysis tube, Prolabo) whose pores are permeable to the uncoupled molecules (MW <12,000 to 14,000 Da). To maximize the removal of uncoupled molecules, the 1st dialysis solution comprises 1/3 of DMF, 1/3 of methanol and 1/3 of $10^{-2}$ M phosphate buffer containing $10^{-3}$ M $CaCl_2$. Two further dialysis are performed for 24 h with $10^{-2}$ M phosphate buffer solution containing $10^{-3}$ M $CaCl_2$. The role of the $CaCl_2$ is to make the conjugates more soluble through interaction of the $Ca^{2+}$ ions with the aliphatic chains. However, this buffer can be replaced with a 10 mM guanidine buffer, pH 7.

The resulting conjugates are designated R-PL (R=hapten).

VI. Acetylation of the Farnesylcysteine or Thiol Conjugates Coupled via Carbodiimide The pH of the conjugates is brought to 10 with 1 M sodium hydroxide solution. A mixture of 4 μl of acetic anhydride (Prolabo) and 500 μl of anhydrous DMSO is then added. The reaction can be neutralized by the addition of 40 μl of 1 M NaOH.

The conjugates are then dialyzed against water.

The resulting conjugates are designated R-PL-Nac (R=hapten, Nac=N-acetylated).

VII. Cholesterol or Retinoic Acid Conjugates by Adsorption

Retinoic acid:

40 mg of hapten are solubilized in 2 ml of anhydrous methanol and 2 ml of anhydrous DMF containing 1 μl of radioactive tracer (cholesterol: ref. NET 725, Dupont de Nemours). 80 mg of PL dissolved in 2 ml of 1.5 M acetate buffer are then added dropwise. After thorough stirring, the conjugates are purified by dialysis. The first dialysis solution consists of a mixture of 1/3 of methanol, 1/3 of DMF and 1/3 of water. The following two solutions consist solely of water.

The resulting conjugates are designated R-PL (R=hapten).

VIII. Hexamethylene Diisocyanate Conjugates 5 mg of 2-methoxyestradiol are taken up with 1 ml of DMSO and 1 μl of radioactive hormone (progesterone: ref. N381, Dupont de Nemours). 10 mg of PL dissolved in 1 ml of 0.2 M phosphate buffer, pH 10, and 50 μl of hexamethylene diisocyanate (Fluka) are added. The pH is adjusted to 10 with 1 N sodium hydroxide solution.

The protocol is the same for progesterone except that the starting materials are 40 mg of progesterone, 80 mg of PL and 200 μl of hexamethylene diisocyanate.

The conjugates are purified by dialysis; the 1st solution consists of a DMF/DMSO/water mixture and the following two consist of water.

The resulting conjugates are designated R-PL (R=hapten).

In general terms, the small equipment in which the coupling reactions and the purifications of the hydrophobic conjugates are performed is delipidated by rinsing with methanol and drying in order to avoid any external contamination with lipids. Furthermore, in the synthesis of the conjugates containing a hapten which possesses a thiol group (cysteine, homocysteine, methionine, etc.), a few grains of the corresponding uncoupled hapten are added after dialysis.

In the Examples which follow, the polylysine conjugates were synthesized by the procedure described above using polylysine marketed by Sigma under the reference P 7890. By way of indication, the coupling ratios of the conjugates used in the Examples are reported in the Table below:

| | | | |
|---|---|---|---|
| αtoco-PL | 23 | Aze-PL-Lin2 | 10, 10 |
| Pro-PL | 8 | Farcys-PL-PO | 30, 30 |
| Farcys-PL-Pal | 8, 8 | Pal-PL-Myr | 25, 25 |
| CHO-PL | 33 | Homocys-PL | 4 |
| Ole-PL-Pal | 5, 5 | GABA-GA-PL | 23 |
| αtoco-PL-Ret | 22, 23 | L-DOPA-GA-PL | 18 |
| Ret-PL | 11 | Homocys-GA-PL | 22 |

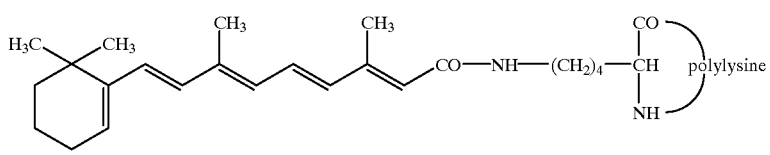

-continued

| | | | |
|---|---|---|---|
| Ole-PL-Laur | 7, 5 | Homocys-G-PL | 5 |
| Tau-GA-PL | 32 | Cys-G-PL | 5 |
| Tau-G-PL | 44 | Met-G-PL | 12 |
| His-G-PL | 5 | Homocys-G-PL | 4 |
| Cys-GA-PL | 10 | Cys-PL-Nac | 3 |
| HW-GA-PL | 41 | Met-PL-Nac | 7 |
| W-GA-PL | 32 | 2ME-PL | 22 |
| Cys-PL-Nac | 2 | PRO-PL | 12 |
| Homocys-PL-Nac | 3 | GABA-G-PL | 10 |
| L-DOPA-G-PL | 4 | Aze-PL-Farcys | 10, 10 |

Coupling ratio is understood as meaning the number of conjugated molecules of hapten(s) per molecule of polylysine. In the case of the bifunctional conjugates, the respective number of conjugated molecules is indicated for each hapten.

EXAMPLE 1

Preparation of a pharmaceutical combination for the treatment of neurological disorders resulting from Lyme disease Numerous neurological diseases are the consequence of known or unknown bacterial and viral infections. *Borrelia burgdorflei* is the etiological agent of Lyme disease. It causes neuropathy in a number of cases.

The following solutions were prepared:

| Solution 1 | | Solution 2 | |
|---|---|---|---|
| Farcys-PL-Pal | 1 | Farcys-PL-Pal | 1 |
| Pal-PL-Myr | 1 | Farcys-PL-Myr | 1 |
| Farcys-PL-Myr | 1 | Pal-PL-Myr | 1 |
| Lin2-PL-Ole | 1 | Aze-PL-Ole | 1 |
| Met-PL-Nac | 1 | Pal-PL-Ole | 1 |
| Cys-PL-Nac | 1 | Farcys-PL-Ole | 1 |
| Homocys-PL-Nac | 1 | PO-PL-Aze | 1 |
| Farcys-PL-Ole | 1 | Ole-PL-Myr | 1 |
| Met-GA-PL | 1 | Stea-PL-Farcys | 1 |
| Pal-PL-Ole | 1 | Ole-PL-Laur | 1 |
| Myr-PL-Ole | 1 | | |
| Tau-GA-PL | 2 | | |
| VitC-PL | 2 | | |
| Tau-G-PL | 2 | | |
| Stea-PL-Farcys | 2 | | |
| ACh-GA-PL | 2 | | |
| αtoco-PL | 2 | | |
| Aze-PL-Ole | 2 | | |

The figure on the right of the monofunctional or bifunctional polylysine conjugate indicates the concentration of hapten(s) in said conjugate in the solution, it being understood that a value of 1 corresponds to a concentration of $10^{-5}$ M. Thus, for the bifunctional conjugate Farcys-PL-Pal:

[Farcys]=$10^{-5}$ M
[Pal]=$10^{-5}$ M

In this way it is possible to determine the final concentration of each hapten in solutions 1 and 2. For example, the final concentration of Farcys in solution 1 is $5.10^{-5}$ M.

Method of Preparation:

The various solutions of monofunctional and bifunctional conjugates, prepared in physiological saline for immediate use, are mixed to give the hapten concentrations indicated above after vortexing and dilution in the respective final solutions 1 and 2. The solutions are subsequently filtered separately on sterile Sartorius filters of pore size 0.22 $\mu$m and are then divided up into individual sterile bottles or made up into individual solutions to be taken orally (mixture with syrup, pure vegetable oil from 1st pressing).

Solutions 1 and 2 are administered alternately by slow intramuscular or subcutaneous injection at a rate of 1 ml of each solution once or twice a day, for example solution 2 twice and solution 1 once every day.

All the patients (n=4) treated according to the protocol described above show a regression of the neuropathy caused by Lyme disease.

EXAMPLE 2

Preparation of a pharmaceutical combination for the treatment of amyotrophic lateral sclerosis Amyotrophic lateral sclerosis (ALS), also called Charcot's disease, is a progressive disease and is one of the triad of degenerative diseases of the nervous system in the elderly, the other two being Alzheimer's and Parkinson's diseases. All three are characterized by a selective vulnerability of a group of neurons which disappear for reasons not yet understood. In fact, the lesions are caused neither by vascular problems nor by inflammatory reactions. In ALS the affected cells are the motor neurons of the anterior horn of the spinal cord and of the motor cranial nuclei: V, VII, IX, XI, XII, and the (corticospinal and corticobulbar) motor tracts, which can be affected in their entirety, causing amyotrophy as a secondary manifestation. The course of the disease is towards a progressive deterioration with the patient becoming bedridden and suffering from a respiratory failure affecting the intercostal and diaphragmatic musculature and rapidly leading to death (within 24 to 26 months, on average, in the majority of cases). ALS occurs in adult men and women between 40 and 60 years of age (2000 new cases per year are reported in France). The incidence of ALS is the same as that of multiple sclerosis (MS) and five times greater than that of Huntington's disease.

The etiology of this disease is still unknown. The prevailing model at present is multifactorial. The disease is said to result from the combined action of a genetic susceptibility (5 to 10% of cases of familial ALS are said to be associated with an autosomal transmission located on chromosome 21), accelerated ageing and exogenous and/or endogenous neurotoxic factors, culminating in the selective destruction of the motor neurons.

The following solutions were prepared:

| Solution 3 | | Solution 4 | |
|---|---|---|---|
| Myr-PL-Pal | 1 | Pal-PL-Ole | 1 |
| Pal-PL-Ole | 1 | Tau-SA-PL or | 1 |
| Myr-PL-Ole | 1 | Tau-GA-PL | |
| Tau-SA-PL or | 1 | αtoco-PL | 3 |
| Tau-GA-PL | | VitC-PL | 1 |
| αtoco-PL | 3 | Homocys-PL-Nac | 4 |
| VitC-PL | 1 | Cys-PL-Nac | 4 |
| Homocys-PL-Nac | 4 | Met-PL-Nac | 4 |
| Cys-PL-Nac | 4 | Farcys-PL-Myr | 1 |
| Met-PL-Nac | 4 | Farcys-PL-Pal | 1 |
| Farcys-PL-Myr | 1 | Farcys-PL-Ole | 1 |
| Farcys-PL-Pal | 1 | Farcys-PL-Stea | 1 |
| Farcys-PL-Ole | 1 | Met-SA-PL or | 4 |
| Farcys-PL-Stea | 1 | Met-GA-PL | |
| Met-SA-PL or | 4 | Homocys-SA-PL or | 4 |
| Met-GA-PL | | Homocys-GA-PL | |
| Homocys-SA-PL or | 4 | Cys-GA-PL | 4 |
| Homocys-GA-PL | | Cys-G-PL | 4 |
| Cys-G-PL | 4 | Met-G-PL | 4 |
| Homocys-G-PL | 4 | Homocys-G-PL | 4 |
| Met-G-PL | 4 | Met-G-PL | 4 |
| CHO-PL | 1 | CHO-PL | 1 |
| 5MT-GA-PL | 1 | W-GA-PL | 2 |

-continued

| Solution 3 | | Solution 4 | |
|---|---|---|---|
| W-GA-PL | 2 | ACh-GA-PL | 4 |
| ACh-GA-PL | 4 | AI = 0.1 mg/ml | |

Method of Preparation: as for Example 1

Solutions 3 and 4 are administered by slow subcutaneous injection at a rate of 0.8 ml of each solution twice a day, or 0.8 ml of solution per day with solutions 3 and 4 being alternated every other day.

A stabilization of the symptomatology is observed in 80% of cases (n=30); an improvement in the symptomatology (regression of the attacks) is even found in 40 to 50% of cases.

EXAMPLE 3

Preparation of a pharmaceutical composition for the treatment of Parkinson's disease This is a degenerative disease of the central nervous system in which the dopaminergic neurons of the nigrostriatal tract are selectively destroyed.

Parkinson's disease is the culmination of an active chronic process starting 20 to 30 years before the disease is expressed, the origin being of a multifactorial nature according to recent theories. It is the result of the combined action of a genetic susceptibility, ageing and exogenous and endogenous neurotoxic factors, culminating in the destruction of the ascending monoaminergic systems. Postmortem analysis of subjects affected by the idiopathic or postencephalitic form reveals the following essential phenomena:

(i) a degeneration of the nigrostriatal bundle results in the collapse of the levels of dopamine (DA) and its metabolites in the neostriatum and a predominant neuronal loss in the pars compacta of the substantia nigra;

(ii) a deficiency of DA in the neurons of the tegmentoventral area (TVA) which are at the origin of the mesocorticolimbic tract and which project onto the nucleus accumbens. A less significant decrease in the number of DA neurons and Lewy bodies is observed in the ventral part of the TVA. The depletion of DA has to reach a certain critical threshold (60% to 80%) before the symptoms of parkinsonism appear, akinesia being the principal symptom related to the degree of depletion of DA;

(iii) the disappearance of neurons in the substantia nigra is accompanied by the release of melanotic pigment and especially the appearance of Lewy bodies, their presence being a customary indicator of this specific neuronal attack.

At the evolutive and individual level, Parkinson's disease is thought to result from the intervention of these different factors, early in life, in subjects who possess a genetic susceptibility expressing itself for example in their antioxidative capacity (glutathion reductase, hydroxylation phenotype . . . ), leading to a reduction of the neuronal pool in the substantia nigra. The physiological loss of neurons associated with age would then culminate in the clinical expression of the disease when 80% of the dopaminergic neurons in the substantia nigra have disappeared.

The following solution was prepared:

| Solution 5 | |
|---|---|
| L-DOPA-G-PL | 5 |
| αtoco-PL | 2 |
| Ole-PL-Farcys | 1 |
| PO-PL-Ole | 1 |
| Myr-PL-Ole | 1 |
| Cys-GA-PL or Cys-SA-PL | 1 |
| Homocys-GA-PL or Homocys-SA-PL | 1 |
| Met-GA-PL or Met-SA-PL | 1 |
| Met-G-PL | 1 |
| Cys-G-PL | 1 |
| Homocys-G-PL | 1 |
| Laur-PL-Ole | 1 |
| GABA-GA-PL | 2 |
| 5MT-GA-PL | 1 |
| Hist-PL | 1 |
| Cys-PL-Nac | 1 |
| Homocys-PL-Nac | 1 |
| Met-PL-Nac | 1 |

Preparation: as for Example 1

Solution 5 is administered by subcutaneous injection at a rate of 0.4 to 0.8 ml of solution every 2 to 3 days.

An improvement in the rigidity, akinesia and trembling is observed in 80% of cases (n=15), with a reduction in the administration of other treatments.

EXAMPLE 4

Preparation of a pharmaceutical combination for the treatment of Huntington's chorea The following solutions were prepared:

| Solution 6 | | Solution 7 | |
|---|---|---|---|
| Myr-PL-Pal | 1 | Cys-GA-PL | 4 |
| Pal-PL-Ole | 1 | Met-GA-PL | 4 |
| Myr-PL-Ole | 1 | Homocys-G-PL | 4 |
| Tau-SA-PL or Tau-GA-PL | 1 | Cys-PL-Nac | 4 |
| αtoco-PL | 3 | Homocys-PL-Nac | 4 |
| VitC-PL | 1 | Met-PL-Nac | 4 |
| Homocys-PL-Nac | 4 | Tau-GA-PL | 1 |
| Cys-PL-Nac | 4 | Tau-G-PL | 1 |
| Met-PL-Nac | 4 | Met-G-PL | 4 |
| Farcys-PL-Myr | 1 | αtoco-PL | 2 |
| Farcys-PL-Pal | 1 | αtoco-PL-Ret | 2 |
| Farcys-PL-Ole | 1 | | |
| Farcys-PL-Stea | 1 | | |
| Met-SA-PL or Met-GA-PL | 4 | | |
| Homocys-SA-PL or Homocys-GA-PL | 4 | | |
| Cys-G-PL | 4 | | |
| Homocys-G-PL | 4 | | |
| Met-G-PL | 4 | | |
| CHO-PL | 1 | | |
| 5MT-GA-PL | 1 | | |
| W-GA-PL | 2 | | |
| ACh-GA-PL | 4 | | |
| Solution 8 | | | |
| Farcys-PL-Ole | 2 | | |
| Aze-PL-Ole | 1 | | |
| Aze-PL-PO | 1 | | |
| Met-PL-Nac | 2 | | |
| Cys-PL-Nac | 2 | | |

-continued

| | |
|---|---|
| Homocys-PL-Nac | 2 |
| αtoco-PL | 2 |
| Lin2-PL-Ole | 2 |
| Ret-PL | 1 |
| Ole-PL-Laur | 1 |
| αtoco-PL-Ret | 1 |
| Tau-G-PL | 1 |
| ACh-GA-PL | 1 |
| PRO-PL | 1 |
| GABA-G-PL | 1 |

Preparation: as for Example 1

Solutions 6, 7 and 8 are administered by subcutaneous injection:

either at a rate of 0.6 ml of each solution every day;

or alternately at a rate of 0.6 ml of one solution every two to three days (for example, it is possible to administer solution 6 on the first day, solution 7 on the second day and solution 8 on the third day, etc., or else to administer solution 6 on the first day, solution 7 on the third day and solution 8 on the fifth day, etc.).

In five patients undergoing treatment, a distinct improvement is found in the level of recovery of the memory functions and relational alertness.

EXAMPLE 5

Preparation of a pharmaceutical combination for the treatment of multiple sclerosis In France, more than 50,000 people suffer from multiple sclerosis (MS) and at least 2000 new cases are recorded each year. This disease starts in the young subject, usually between 20 and 40 years of age. Its incidence is 2 to 3 times greater in women than in men. The symptoms are variable. They can take the following forms: visual disorders, muscular weakness, loss of coordination of movements or contractures, etc. They all reflect a deterioration of the central nervous conduction. They can disappear or decrease and then reappear in a more serious form. The disease usually takes a cyclic course, resulting in progressive invalidity, but the clinical forms are very polymorphous. It is an incapacitating disease which is very expensive in terms of clinical follow-up, symptomatic treatment and financial liability.

MS is a multifactorial disease involving factors associated with the environment, a genetic predisposition and immunological disorders. The prevailing model can be summarized as follows: a predisposed subject (high frequency of the following antigens of the HLA system: A3, B7, DR2DW2, DQB 1 and DR4) encounters an exogenous, probably viral and/or bacterial factor. A long and totally silent phase of latency ensues, followed by the development of reactions, to some extent autoimmune, which are directed against myelin and the producing cell, the oligodendrocyte. These disorders result in demyelinizing lesions of the central nervous system (CNS). The multiplicity and complexity of the factors involved in MS constitute obstacles to the understanding of its etiology. It is for this reason, despite numerous studies, that MS is still not understood.

The following solutions were prepared:

| Solution 9 | | Solution 10 | |
|---|---|---|---|
| Farcys-PL-Ole | 2 | Farcys-PL-Pal | 1 |
| PO-PL-Ole | 2 | Farcys-PL-Myr | 1 |
| Aze-PL-Ole | 2 | Pal-PL-Myr | 1 |
| Aze-PL-PO | 2 | Aze-PL-Ole | 1 |
| Met-PL-Nac | 2 | Pal-PL-Ole | 1 |
| Homocys-PL-Nac | 2 | Farcys-PL-Ole | 1 |
| αtoco-PL | 2 | PO-PL-Aze | 1 |
| VitC-PL | 1 | Ole-PL-Myr | 1 |
| Tau-GA-PL | 2 | Stea-PL-Farcys | 1 |
| Lin2-PL-Ole | 2 | Ole-PL-Laur | 1 |
| CHO-PL | 1 | | |
| Ole-PL-Laur | 1 | | |
| 5MT-GA-PL | 1 | | |
| Tau-G-PL | 2 | | |
| ACh-GA-PL | 2 | | |

| Solution 11 | | Solution 12 | |
|---|---|---|---|
| Farcys-PL-Ole | 2 | Farcys-PL-Ole | 2 |
| Aze-PL-Ole | 1 | Aze-PL-Ole | 1 |
| Aze-PL-PO | 1 | Aze-PL-PO | 1 |
| Met-PL-Nac | 2 | αtoco-PL | 2 |
| Cys-PL-Nac | 2 | VitC-PL | 1 |
| Homocys-PL-Nac | 2 | Tau-GA-PL | 2 |
| αtoco-PL | 2 | Lin2-PL-Ole | 2 |
| Lin2-PL-Ole | 2 | CHO-PL | 1 |
| Ret-PL | 1 | Laur-PL-Ole | 1 |
| Ole-PL-Laur | 1 | AI = 0.1 mg/ml | |
| αtoco-PL-Ret | 1 | | |
| Tau-G-PL | 1 | | |
| ACh-GA-PL | 1 | | |
| PRO-PL | 1 | | |
| GABA-G-PL | 1 | | |

Preparation: as for Example 1

The administration (by subcutaneous injection) of solutions 9, 10, 11 and 12 varies according to the clinical form of multiple sclerosis (MS).

a) In the case of an attack or deterioration of MS, at least two of solutions 9, 10 and 11 are used alternately at a rate of 0.5 ml to 1 ml of these solutions once or twice a day, or else at a rate of 0.5 ml to 1 ml of these solutions every 2–3 days or once a week. For example, from day 1 to 8 of treatment, solutions 9 and 10 are administered alternately once or twice a day. From day 8 to 10 of treatment, solutions 9 and 11 are administered alternately once a day. From day 10 to 20 of treatment, solutions 9 and 11 are administered alternately every two days. Then, after day 20 of treatment, solutions 9, 10 and 11 are used alternately every 2–3 days.

In all the cases (n=15) of an attack or deterioration of MS treated by the above protocol since June 1994, a 100% regression of the symptomatology has been observed.

b) In the case of the chronic disease or the resumption of the sequelae, solutions 9, 11 and 12 are administered alternately at a rate of 0.5 ml to 0.8 ml per day. For example, one solution is administered each day, in the morning or evening.

A significant regression of the symptomatology is observed in 80% of treated cases (n=250).

EXAMPLE 6

Preparation of a pharmaceutical composition for the treatment of epilepsy

Essential epilepsy can comprise different clinical forms and electroencephalo-graphic seizures, ranging from absence epilepsy to grand mal epilepsy.

The following solution was prepared:

| Solution 13 | |
|---|---|
| GABA-G-PL | 4 |
| PO-PL-Aze | 2 |
| Pal-PL-Farcys | 1 |
| Myr-PL-Farcys | 1 |
| W-GA-PL | 1 |
| Ole-PL-Pal | 1 |
| Myr-PL-Ole | 1 |
| αtoco-PL | 2 |
| Aze-PL-Lin2 | 2 |

Preparation: as for Example 1

Solution 13 is administered by subcutaneous injection at a rate of 0.6 ml of solution 2 to 3 times a week.

The two patients treated reduced their conventional medications (Zarontin®, Dépamide®, etc.) to no major disadvantage.

EXAMPLE 7

Preparation of a pharmaceutical composition for the treatment of essential migraine This has no apparent cause. It presents with or without aura. It is associated with a vasogenic reflex involving serotonin and its derivatives.

The following solution was prepared:

| Solution 14 | |
|---|---|
| HW-GA-PL | 3 |
| W-GA-PL | 3 |
| 5MT-GA-PL | 3 |
| αtoco-PL | 2 |
| Cys-GA-PL | 1 |
| Met-GA-PL | 1 |
| Homocys-GA-PL | 1 |

Preparation: as for Example 1

Solution 14 is administered by subcutaneous injection at a rate of 0.8 ml of solution 2 to 3 times a day in the event of an attack. For a permanent migraine condition, it is preferable to administer 0.8 ml of solution every 2 to 3 days.

In three cases treated, a cessation of the attack or an alleviation of the migraine condition is observed.

EXAMPLE 8

Preparation of a pharmaceutical combination for the treatment of polyarthritis

Rheumatoid polyarthritis (RP) is a disease of the autoimmune type whose etiology is still not understood.

Inflammatory rheumatism has an appreciable effect on the joints, with incapacitating deformations and intense pain.

No specific treatment for RP is known. The main drugs used, namely gold salts, D-penicillamine, sulfasalazine, methotrexate, antimalarials, non-steroidal anti-inflammatories, immunodepressants and immunostimulants, act either on the immunity or on the inflammation, but these drugs have limits and disadvantages:

in the short term their efficacy is partial and only in certain patients;

in the long term there is no proof of their efficacy, but there is proof of numerous side effects (gastrointestinal disorders, immunodepression, etc.);

they are not harmless, sometimes causing serious illnesses.

The following solutions were prepared:

| Solution 15 | | Solution 16 | |
|---|---|---|---|
| Farcys-PL-Pal | 1 | Farcys-PL-Pal | 1 |
| Pal-PL-Myr | 1 | Farcys-PL-Myr | 1 |
| Farcys-PL-Myr | 1 | Pal-PL-Myr | 1 |
| Lin2-PL-Ole | 1 | Aze-PL-Ole | 1 |
| Met-PL-Nac | 1 | Pal-PL-Ole | 1 |
| Cys-PL-Nac | 1 | Farcys-PL-Ole | 1 |
| Homocys-PL-Nac | 1 | PO-PL-Aze | 1 |
| Farcys-PL-Ole | 1 | Ole-PL-Myr | 1 |
| Met-GA-PL | 1 | Stea-PL-Farcys | 1 |
| Pal-PL-Ole | 1 | Ole-PL-Laur | 1 |
| Myr-PL-Ole | 1 | | |
| Tau-GA-PL | 2 | | |
| VitC-PL | 2 | | |
| Tau-G-PL | 2 | | |
| Stea-PL-Farcys | 2 | | |
| ACh-GA-PL | 2 | | |
| αtoco-PL | 2 | | |
| Aze-PL-Ole | 2 | | |

| Solution 17 | |
|---|---|
| Farcys-PL-Pal | 1 |
| Pal-PL-Myr | 1 |
| Farcys-PL-Myr | 1 |
| Farcys-PL-Ole | 1 |
| Myr-PL-Ole | 1 |
| Stea-PL-Farcys | 1 |
| ACh-GA-PL | 2 |
| αtoco-PL | 2 |
| AI = 0.1 mg/ml | |

Preparation: as for Example 1

The subcutaneous administration of solutions 15, 16 and 17 varies according to the clinical form of rheumatoid polyarthritis.

a) In a period of attack or deterioration, solutions 15 and 16 are used at a rate of 0.1 ml to 0.5 ml of each solution in a mixture, once or twice a day.

b) In a chronic phase, the following are used alternately:
either solutions 15 and 16 mixed together
or solutions 16 and 17 mixed together at a rate of 0.1 ml to 0.5 ml of each solution every 2, 3 or 4 days or every week.

In the subjects treated (n=150), the rheumatoid polyarthritis is found to take a favorable course in 80% of cases, even for old complaints resistant to other therapies.

Bibliographic References

1. Daverat et al., J. Neuroimmunol.: 22, 129–134 (1989)
2. Amara et al., AIDS: 8, 711–713 (1994)
3. Maneta-Peyret et al., Neuroscience Letters: 80, 235–239 (1987)
4. Brochet et al., Current Concepts in Multiple Sclerosis: 10, 97–102 (1991)
5. Boullerne et al., Satellite Symposium to 17th ENA Meeting, Prague, September 1994
6. Buttke et al., Immunology Today: 15, 7–10 (1994)
7. Hunter et al., Neurochem. Res.: 10, 1645–1652 (1985)
8. Korpela et al., J. Neurol. Sci.: 91, 79–84 (1989)
9. Roederer et al., Pharmacol.: 46, 121–129 (1993)
10. Staal et al., The Lancet: 339, 909–912 (1992)
11. Geffard et al., Science: 229, 77–79 (1985)
12. Souan et al., Neuroscience Letters: 64, 23–28 (1986)

13. Geffard et al., J. Neurochem.: 44, 1221–1228 (1985)
14. Geffard et al., Neurochem. Int.: 7, 403–413 (1985)
15. Seguela et al., Proc. Natl. Acad. Sci. USA: 81, 3888–3892 (1984)
16. Geffard et al., C.R. Acad. Sci. Paris: 295, 797–802 (1982)
17. Geffard et al., Brain Res.: 294, 161–165 (1984)
18. Chagnaud et al., Polycyclic Aromatic compounds: 663–672 (1993) (Ph. Garrigues and M. Lamotte Eds., Gordon and Breach Science Publishers)
19. Chagnaud et al., Polycyclic Aromatic compounds: 1119–1126 (1993) (Ph. Garrigues and M. Lamotte Eds., Gordon and Breach Science Publishers)
20. Chagnaud et al., Anti-cancer drugs: 5, 361–366 (1994)
21. Campistron et al., Brain Research: 365, 179–184 (1986)

I claim:

1. A monofunctional conjugate between polylysine and a molecule selected from the group consisting of:
   a) a hydrophobic hormone;
   b) an antioxidant molecule selected from the group consisting of vitamin A, vitamin C, vitamin E and their derivatives which retain the antioxidant properties of said antioxidant molecule;
   c) an amino acid of the formula $R_3$—CH($NH_2$)—COOH in which $R_3$ is hydrogen, an imidazole-5-ylmethyl group or an aminopropyl group;
   an amino($C_1$–$C_5$)alkylsulfonic or sulfinic acid;
   carnitine or carnosine;
   a diamine of the formula $H_2N$—A—$NH_2$ in which A is a ($C_1$–$C_6$)alkylene or a group —($CH_2$)$_m$ NH—B—($CH_2$)$_p$—, in which m and p independently of one another are integers of from 1 to 5 and B is a bond or a group —($CH_2$)$_n$13 NH—, n being an integer of from 1 to 5.

2. A polyfunctional conjugate between at least one polylysine molecule and at least two molecules selected from the group consisting of:
   a) saturated or unsaturated, linear or branched fatty (di) acids comprising from 4 to 24 carbon atoms;
   isoprenoids having 6 to 20 carbon atoms and bonded to a cysteine;
   cholesterol and hydrophobic hormones;
   b) an antioxidant molecule selected from the group consisting of vitamin A, vitamin C, vitamin E and their derivatives which retain the antioxidant properties of said antioxidant molecule;
   cysteine and its derivatives of the formula $R_1S$—$R_2$—CH($NH_2$)—COOH in which $R_1$ is H or $CH_3$ and $R_2$ is a $C_1$–$C_3$-alkylene;
   c) indolealkylamines;
   catecholamines;
   amino acids of the formula $R_3$—CH($NH_2$)—COOH in which $R_3$ is hydrogen, an imidazole-5-ylmethyl group, a carboxymethyl group or an aminopropyl group;
   amino($C_1$–$C_5$)alkylsulfonic or sulfinic acids;
   carnitine or carnosine;
   diamines of the formula $H_2N$—A—$NH_2$ in which A is a ($C_1$–$C_6$)alkylene or a group —($CH_2$)$_m$ —NH—B—($CH_2$)$_p$—, in which m and p independently of one another are integers of from 1 to 5 and B is a bond or a group —($CH_2$)$_n$—NH—, n being an integer of from 1 to 5;
   acetylcholine;
   γ-aninobutyric acid.

3. The conjugate as claimed in claim 2 which is a bifunctional conjugate.

4. A pharmaceutical composition or combination which comprises therapeutically effective amounts of:
   a) at least one monofunctional and/or polyfunctional conjugate between polylysine and one or more molecules selected from the group consisting of:
      saturated or unsaturated, linear or branched fatty (di) acids comprising from 4 to 24 carbon atoms,
      isoprenoids having 6 to 20 carbon atoms and bonded to a cysteine, and
      cholesterol and hydrophobic hormones;
   b) at least one monofunctional and/or polyfunctional conjugate between polylysine and one or more antioxidant molecules selected from the group consisting of:
      vitamin A, vitamin C, vitamin E or one of their derivatives which retains the antioxidant properties of said antioxidant molecules, and
      cysteine and its derivatives of the formula $R_1S$—$R_2$—CH($NH_2$)—COOH in which $R_1$ is H or $CH_3$ and $R_2$ is a $C_1$–$C_3$-alkylene; and
   c) at least one monofunctional and/or polyfunctional conjugate between polylysine and one or more molecules selected from the group consisting of:
      indolealkylamines,
      catecholamines,
      amino acids of the formula $R_3$—CH($NH_2$)—COOH in which $R_3$ is hydrogen, an imidazol-5-ylmethyl group, a carboxymethyl group or an aminopropyl group,
      amino ($C_1$–$C_5$)alkylsulfonic or sulfinic acids,
      carnitine or carnosine,
      diamines of the formula $H_2N$—A—$NH_2$ in which A is a ($C_1$–$C_6$)alkylene or a group —($CH_2$)$_m$ —NH—B—($CH_2$)$_p$—, in which m and p independently of one another are integers ranging from 1 to 5 and B is a bond or a group —($CH_2$)$_n$— NH—, n is an integer of from 1 to 5,
      acetylcholine, and
      γ-aminobutyric acid.

5. A pharmaceutical composition or combination as claimed in claim 4, which further comprises an anti-idiotypic monoclonal antibody.

6. A pharmaceutical composition or combination as claimed in claim 5, wherein said monofunctional conjugate of component a) is a conjugate between polylysine and a fatty (di)acid.

7. A pharmaceutical composition or combination as claimed in claim 6, wherein the fatty (di)acid is selected from the group consisting of myristic acid, palmitic acid, stearic acid, oleic acid and azelaic acid.

8. A pharmaceutical composition or combination as claimed in claim 5, wherein said polyfunctional conjugate of component a) is a bifunctional conjugate in which at least one of the molecules is a fatty (di)acid.

9. A pharmaceutical composition or combination as claimed in claim 8, wherein the fatty (di)acid is selected from the group consisting of myristic acid, palmitic acid, stearicacid, oleic acid and azelaic acid.

10. A pharmaceutical composition or combination as claimed in claim 4, wherein said monofunctional conjugate of component a) is a conjugate between polylysine and a fatty (di)acid.

11. A pharmaceutical composition or composition as claimed in claim 10, wherein the fatty (di)acid is selected from the group consisting of myristic acid, palmitic acid, stearic acid, oleic acid and azelaic acid.

12. A pharmaceutical composition or combination as claimed in claim 4, wherein said polyfunctional conjugate of component a) is a bifunctional conjugate in which at least one of the molecules is a fatty (di)acid.

13. A pharmaceutical composition or combination as claimed in claim 12, wherein the fatty (di)acid is selected from the group consisting of myristic acid, palmitic acid, stearic acid, oleic acid and azelaic acid.

14. A pharmaceutical combination as claimed in claim 4, which comprises, in four individual packs:

a) an effective amount of a solution of the following conjugates: Farcys-PL-Ole, PO-PL-Ole, Aze-PL-Ole, Aze-PL-PO, Met-PL-Nac, Homocys-PL-Nac, αtoco-PL, VitC-PL, Tau-GA-PL, Lin2-PL-Ole, CHO-PL, Ole-PL-Laur, 5MT-GA-PL, Tau-G-PL and ACh-GA-PL;

b) an effective amount of a solution of the following conjugates: Farcys-PL-Pal, Farcys-PL-Myr, Pal-PL-Myr, Aze-PL-Ole, Pal-PL-Ole, Farcys-PL-Ole, PO-PL-Aze, Ole-PL-Myr, Stea-PL-Farcys and Ole-PL-Laur;

c) an effective amount of a solution of the following conjugates: Farcys-PL-Ole, Aze-PL-Ole, Aze-PL-PO, Met-PL-Nac, Cys-PL-Nac, Homocys-PL-Nac, αtoco-PL, Lin2-PL-Ole, Ret-PL, Ole-PL-Laur, αtoco-PL-Ret, Tau-G-PL, ACh-GA-PL, PRO-PL and GABA-G-PL; and d) an effective amount of a solution of the following conjugates: Farcys-PL-Ole, Aze-PL-Ole, Aze-PL-PO, αtoco-PL, VitC-PL, Tau-GA-PL, Lin2-PL-Ole, CHO-PL and Laur-PL-Ole;

and wherein:

Farcys is farnesylcysteine; PL is polylysine; Ole is oleic acid; PO is palmitoleic acid; Aze is azelaic acid; Met is methionine; Nac is N-acetylated; Homocys is homocysteine; αtoco is α-tocopherol; VitC is ascorbic acid; Tau is taurine; GA is glutaric anhydride; Lin2 is α-linoleic acid; CHO is cholesterol; Laur is lauric acid; 5MT is 5-methoxytryptamine; G is reduced glutaraldehyde; ACh is acetylcholine; Pal is palmitic acid; Myr is myristic acid; Stea is stearic acid; Cys is cysteine; Ret is retinoic acid; PRO is progesterone; and GABA is γ-aminobutyric acid.

15. A pharmaceutical combination as claimed in claim 14, wherein solution d) further comprises an anti-idiotypic monoclonal antibody.

16. A method of treating multiple sclerosis which comprises administering to a subject in need thereof effective amounts of at least two of the following solutions:

a) a solution of the following conjugates: Farcys-PL-Ole, PO-PL-Ole, Aze-PL-Ole, Aze-PL-PO, Met-PL-Nac, Homocys-PL-Nac, αtoco-PL, VitC-PL, Tau-GA-PL, Lin2-PL-Ole, CHO-PL, Ole-PL-Laur, 5MT-GA-PL, Tau-G-PL and ACh-GA-PL;

b) a solution of the following conjugates: Farcys-PL-Pal, Farcys-PL-Myr, Pal-PL-Myr, Aze-PL-Ole, Pal-PL-Ole, Farcys-PL-Ole, PO-PL-Aze, Ole-PL-Myr, Stea-PL-Farcys and Ole-PL-Laur;

c) a solution of the following conjugates: Farcys-PL-Ole, Aze-PL-Ole, Aze-PL-PO, Met-PL-Nac, Cys-PL-Nac, Homocys-PL-Nac, αtoco-PL, Lin2-PL-Ole, Ret-PL, Ole-PL-Laur, αtoco-PL-Ret, Tau-G-PL, ACh-GA-PL, PRO-PL and GABA-G-PL; and d) a solution of the following conjugates: Farcys-PL-Ole, Aze-PL-Ole, Aze-PL-PO, αtoco-PL, VitC-PL, Tau-GA-PL, Lin2-PL-Ole, CHO-PL and Laur-PL-Ole, and of an anti-idiotypic antibody;

and wherein:

Farcys is farnesylcysteine; PL is polylysine; Ole is oleic acid; PO is palmitoleic acid; Aze is azelaic acid; Met is methionine; Nac is N-acetylated; Homocys is homocysteine; αtoco is α-tocopherol; VitC is ascorbic acid; Tau is taurine; GA is glutaric anhydride; Lin2 is α-linoleic acid; CHO is cholesterol; Laur is lauric acid; 5MT is 5-methoxytryptamine; G is reduced glutaraldehyde; ACh is acetylcholine; Pal is palmitic acid; Myr is myristic acid; Stea is stearic acid; Cys is cysteine; Ret is retinoic acid; PRO is progesterone; and GABA is γ-aminobutyric acid.

* * * * *